United States Patent
Radin et al.

(10) Patent No.: US 8,273,083 B2
(45) Date of Patent: Sep. 25, 2012

(54) UNIVERSAL CELL CARRIER

(75) Inventors: Andrew M. Radin, Palo Alto, CA (US); Thomas B. Eby, Mountain View, CA (US); Vera S. Boudtchenka, Mountain View, CA (US); Jennifer Teng, Saratoga, CA (US); John P. Goetz, Aptos, CA (US); John E. Crowe, Menlo Park, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1312 days.

(21) Appl. No.: 11/962,913

(22) Filed: Dec. 21, 2007

(65) Prior Publication Data

US 2009/0163914 A1 Jun. 25, 2009

(51) Int. Cl.
*A61B 18/14* (2006.01)
(52) U.S. Cl. .............. 606/41; 206/363; 607/119
(58) Field of Classification Search .......... 606/41, 606/27; 206/363; 607/119, 129
See application file for complete search history.

(56) References Cited

U.S. PATENT DOCUMENTS

| | | | | |
|---|---|---|---|---|
| 4,163,496 | A | * | 8/1979 | Dogliotti ............. 206/538 |
| 4,204,738 | A | * | 5/1980 | Tillotson ............. 439/369 |
| 4,892,520 | A | | 1/1990 | Gilbaugh |
| 4,946,440 | A | | 8/1990 | Hall |
| 5,152,293 | A | | 10/1992 | Vonesh et al. |
| 5,916,213 | A | * | 6/1999 | Haissaguerre et al. ...... 606/41 |
| 5,921,924 | A | | 7/1999 | Avitall |
| 6,314,962 | B1 | | 11/2001 | Vaska et al. |
| 6,645,202 | B1 | | 11/2003 | Pless et al. |
| 6,689,128 | B2 | | 2/2004 | Sliwa, Jr. et al. |
| 6,701,931 | B2 | | 3/2004 | Sliwa, Jr. et al. |
| 6,719,755 | B2 | | 4/2004 | Sliwa, Jr. et al. |
| 6,752,805 | B2 | | 6/2004 | Maguire et al. |
| 6,792,306 | B2 | | 9/2004 | Henley et al. |
| 6,805,128 | B1 | | 10/2004 | Pless et al. |
| 6,805,129 | B1 | | 10/2004 | Pless et al. |
| 6,840,936 | B2 | | 1/2005 | Sliwa, Jr. et al. |
| 6,858,026 | B2 | | 2/2005 | Sliwa, Jr. et al. |
| 6,971,394 | B2 | | 12/2005 | Sliwa, Jr. et al. |
| 7,052,493 | B2 | | 5/2006 | Vaska et al. |
| 2004/0260281 | A1 | | 12/2004 | Baxter, III et al. |
| 2005/0033274 | A1 | | 2/2005 | Pless et al. |
| 2005/0085731 | A1 | | 4/2005 | Miller et al. |
| 2006/0184167 | A1 | | 8/2006 | Vaska et al. |
| 2007/0293792 | A1 | | 12/2007 | Sliwa et al. |
| 2008/0183166 | A1 | * | 7/2008 | Miller ............. 606/41 |

* cited by examiner

*Primary Examiner* — Michael Peffley
*Assistant Examiner* — Samantha Good
(74) *Attorney, Agent, or Firm* — Dykema Gossett PLLC (57) ABSTRACT

A carrier for an ablation element is provided. The carrier includes a plurality of walls defining a receiving portion configured to receive at least a portion of an ablation element. A plurality of connection formations are disposed on an exterior surface of least one of the plurality of walls. Each of the plurality of connection formations is disposed at a different vertical position of the carrier. A device for epicardial ablation is also provided. The device includes a plurality of carriers disposed adjacent to each other. Each carrier includes a plurality of walls defining a receiving portion configured to receive at least a portion of an ablation element. A plurality of connection formations are disposed on an exterior surface of at least one of the plurality of walls of each carrier. Each of the plurality of connection formations is disposed at a different vertical position of a carrier.

19 Claims, 5 Drawing Sheets

UNIVERSAL CELL CARRIER

BACKGROUND OF THE INVENTION a. Field of the Invention

The instant invention is directed toward a universal cell carrier, including a universal cell carrier for housing an ablation element, such as for use in an epicardial ablation device.

b. Background Art

In a normal heart, contraction and relaxation of the heart muscle (myocardium) takes place in an organized fashion as electrochemical signals pass sequentially through the myocardium from the sinoatrial (SA) node located in the right atrium to the atrialventricular (AV) node and then along a well defined route which includes the His-Purkinje system into the left and right ventricles. Atrial fibrillation results from disorganized electrical activity in the heart muscle, or myocardium. An increasingly common medical procedure for the treatment of certain types of cardiac arrhythmia and atrial arrhythmia involves the ablation of tissue in the heart to cut off the path for stray or improper electrical signals.

Ablation may be performed either from within the chambers of the heart (endocardial ablation) using endovascular devices (e.g., catheters) introduced through arteries or veins, or from outside the heart (epicardial ablation) using devices introduced into the chest. The ablation devices are used to create elongated transmural lesions—that is, lesions extending through a sufficient thickness of the myocardium to block electrical conduction—which form the boundaries of the conductive corridors in the atrial myocardium. The ablation devices create lesions at particular points in the cardiac tissue by physical contact of the cardiac tissue with an ablation element and the application of energy.

One difficulty in obtaining an adequate ablation lesion is the constant movement of the heart, especially when there is an erratic or irregular heart beat. Another difficulty in obtaining an adequate ablation lesion is retaining uniform contact with the cardiac tissue across the entire length of the ablation element surface. Without sufficiently continuous and uniform contact, the associated ablation lesions may not be adequate.

An epicardial ablation device may be used to create uniform, continuous, linear lesions during cardiac ablation. The device may be positioned securely around a patient's atrium while the ablation elements apply energy (e.g., high intensity focused ultrasound energy) to the targeted tissue. The ablation elements are retained by a cell carrier. In a conventional epicardial ablation device, there are any number of unique cell carriers that must be produced for use in a single epicardial ablation device. For example, the tops (e.g., covers) of mid cell carriers must be produced with varying heights in order to provide varying clearances for elements (e.g., wires, tubes) disposed adjacent the cell carrier. In addition to producing a number of unique tops for mid cell carriers, a unique distal cell carrier and unique proximal cell carrier must be produced for use in a single epicardial ablation device. Distal and proximal cell carriers must each be configured to provide for attachment of a leash and an entry point for a fluid tube in a proper orientation that may still allow for sufficient shaping of the device.

BRIEF SUMMARY OF THE INVENTION

It is desirable to be able to reduce the number of unique parts that need to be manufactured to produce cells of varying heights in an ablation device.

Thus, there remains a need for a universal cell carrier that may be easily and inexpensively modified to provide for varying heights for mid cells and/or to provide the features required in distal or proximal cell carriers.

A carrier for an ablation element is provided. The carrier includes a plurality of walls defining a receiving portion configured to receive at least a portion of an ablation element. A plurality of connection formations are disposed on an exterior surface of least one of the plurality of walls. Each of the plurality of connection formations is disposed at a different vertical position of the carrier. A top may also be provided that is configured for connection to the carrier. The top may include a plurality of legs extending inwardly, and the legs may be configured for connection to one of the plurality of connection formations. The top may, therefore, be connected at various connection formations disposed on the carrier to provide a variable space between the carrier and the top.

A device for epicardial ablation is also provided. The device includes a plurality of carriers disposed adjacent to each other. Each carrier includes a plurality of walls defining a receiving portion configured to receive at least a portion of an ablation element. A plurality of connection formations are disposed on an exterior surface of at least one of the plurality of walls of each carrier. Each of the plurality of connection formations is disposed at a different vertical position of each carrier. A top may also be provided that is configured for connection to each carrier. Each top may include a plurality of legs extending inwardly, and the legs may be configured for connection to one of the plurality of connection formations on each carrier. Each top may, therefore, be connected at various connection formations disposed on each carrier in order to provide a variable space between each carrier and each top.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
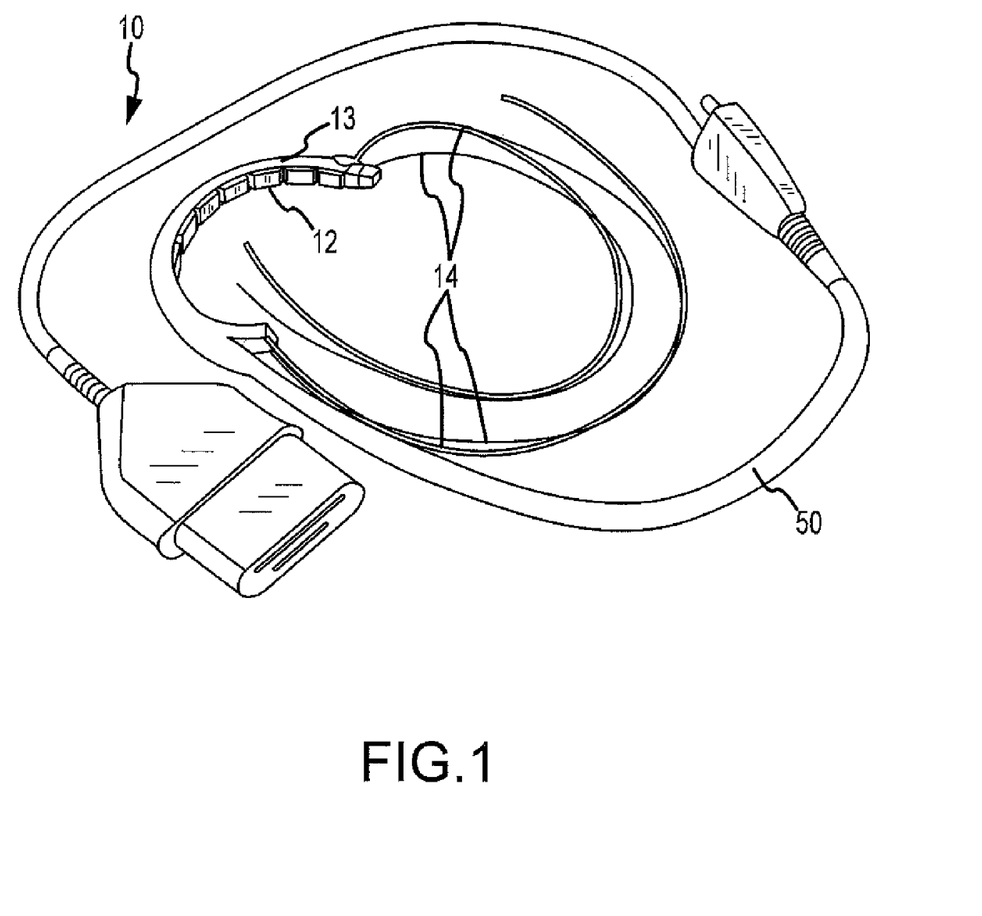
FIG. 1 is a perspective view of a device including a carrier in accordance with an embodiment of the invention.

Referring now to FIG. 1, an epicardial ablation device 10 is illustrated. Device 10 may comprise a series of cells 12 at a first end. Each cell 12 may be movable within a lumen in a body 13. The body 13 may form two suction channels to adhere device 10 to the target tissue. The body 13 may have a curved form and may be made of a flexible material to allow body 13 to form a substantially closed loop. However, it is understood by those of ordinary skill in the art that body 13 may be shaped in any other manner and remain within the spirit and scope of the invention. Body 13 may be connected (e.g., locked) to itself to encircle at least a portion of the heart (e.g., the pulmonary veins) for creating a continuous lesion.

Although the device has been described in connection with creating a continuous lesion around the pulmonary veins, it is understood by those of ordinary skill in the art that the device may also be used for creating other lesions beneficial in treating electrophysiological conditions (e.g., ablating partially around the pulmonary veins or at other locations). The device should not be limited to creating lesions completely around the pulmonary veins.

Body 13 may include elongate elements, such as leashes 14 at both ends. In an embodiment, leashes 14 may comprise braided cable or stainless steel coextruded with a polymer, for example, PEBAX®. Leash 14 may include a swage ball connected at one end. The swage ball may be provided as a mechanical means of securing leash 14 to cell 12. In an embodiment, the swage ball may comprise stainless steel.

Figure 2:
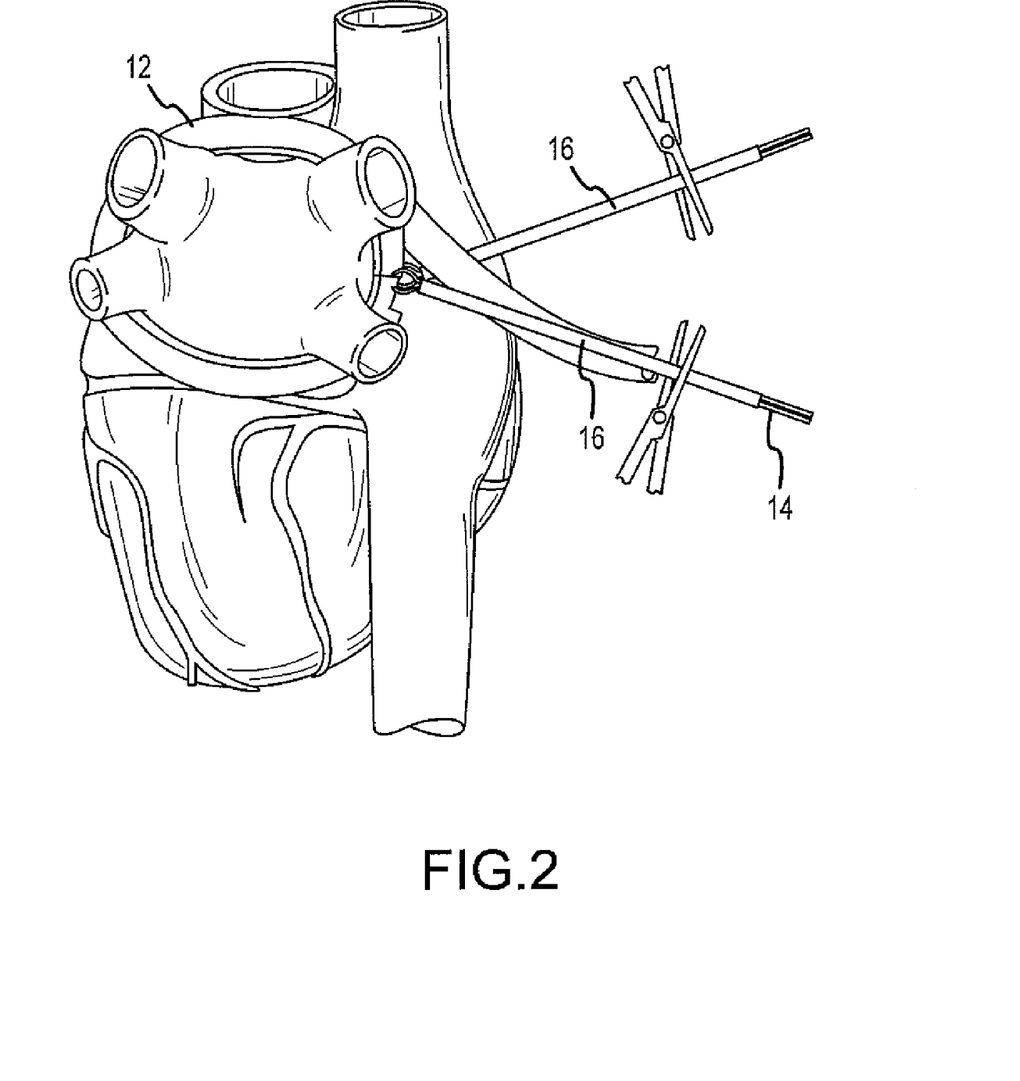
FIG. 2 is a perspective view of a device in FIG. 1 forming a closed loop around the heart.

Leashes 14 may be, for example, tensioned and cinched together to generally connect or lock the ends of the body 13 together using, for example, tourniquets 16 and suture snares in a manner conventional in the art and as generally illustrated in FIG. 2. The body 13 may have two pairs of opposing leashes 14, but may have any number and remain within the spirit and scope of the invention. The leashes 14 may be tensioned using tourniquets 16 to approximate the ends of body 13 so that tensioning the leashes 14 forces the ends substantially together.

An introducer (not shown) may be used to place device 10 around a portion of the heart. For example, an introducer may form a substantially closed loop with a small offset near the distal tip. The introducer may be passed through an incision in the pericardial reflection adjacent the right superior pulmonary vein adjacent the transverse pericardial sinus. The introducer may then be advanced through the transverse pericardial sinus, around the left superior and inferior pulmonary vein, and out through another incision in the pericardial reflection near the right inferior pulmonary vein.

Device 10 may be provided in various sizes, so as to provide for a snug fit around a portion of the heart and accommodate varying patient anatomies. An appropriate size device 10 may then be coupled to the proximal end of the introducer with any suitable connection, such as a snap fit connection. The introducer may then be pulled further to wrap the ablation device 10 around a portion of the heart. The introducer may then be detached from the ablation device 10 by detaching a releasable assembly from the ablation device 10. The releasable assembly may be detached by simply cutting one or more sutures which may hold the releasable assembly to the device 10 or by decoupling the introducer at the same place the introducer is initially coupled to device 10.

Tensioning the leashes 14 may force the ablation device 10 into contact with the epicardial surface. Hemostats or other suitable devices may be used to pinch or crimp tourniquet 16 to connect or lock the ablation device 10 as substantially illustrated in FIG. 2. Device 10 may therefore be positioned against tissue to be ablated and suction may be initiated to hold cells 12 to the tissue to be ablated.

Figure 3:
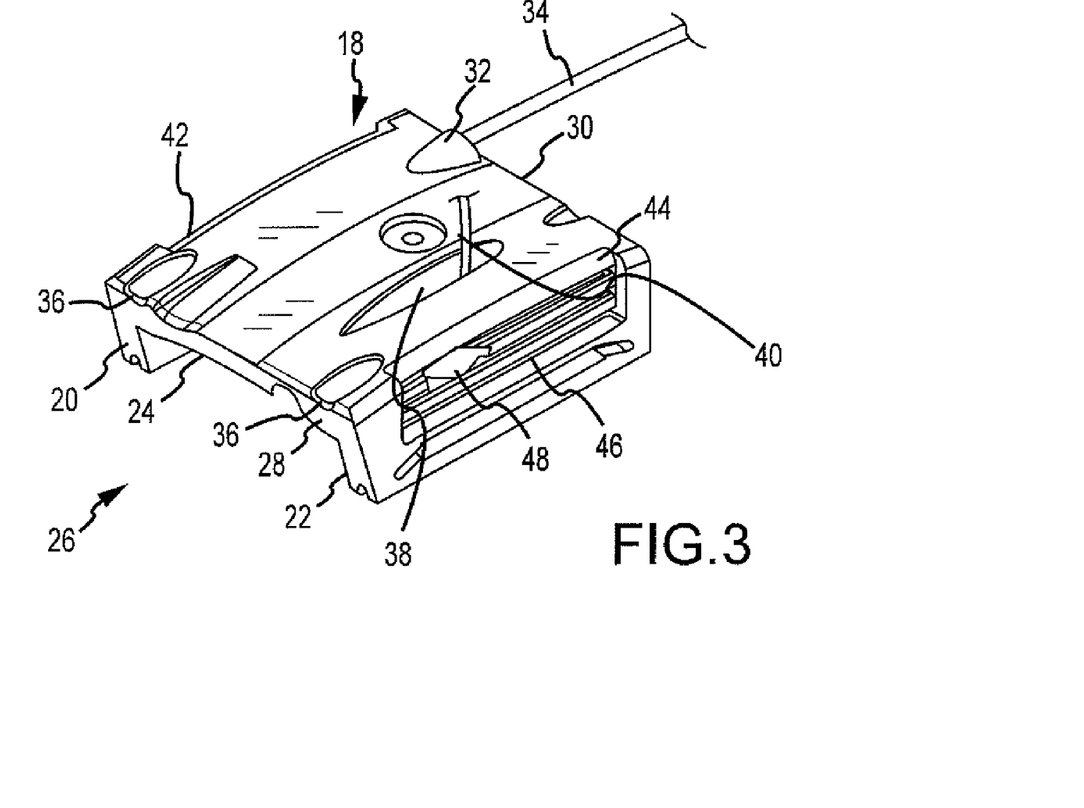
FIG. 3 is a perspective view of a carrier in accordance with an embodiment of the invention.

Each cell 12 may comprise a cell carrier 18. Referring now to FIG. 3, cell carrier 18 is illustrated. Carrier 18 may comprise molded plastic. Carrier 18 may include a first wall 20 and a second wall 22 (i.e., pair of side walls 20, 22) and a third wall 24 (i.e., upper wall 24) connected therebetween. A receiving portion 26 between first and second walls 20, 22 may be configured to receive at least a portion of an ablation element (not shown). The ablation element may comprise an ultrasonic transducer or radio frequency (RF) electrode, although various other ablation elements may be used and remain within the spirit and scope of the invention. The ablation element may be provided to transmit energy (e.g., ultrasound energy) to target tissue. A controller (not shown) may be provided to control delivery of energy. The ablation elements may have a membrane (not shown) that may conform to the required shape to fill the gap between the ablation element and the tissue to be ablated. Each membrane may be fed by an inlet leading to the membrane that provides a fluid, such as saline, to the membrane interface. The source of fluid may, for example, comprise a bag that provides a gravity feed and is coupled to the device with a standard connection such as a standard luer connection. Although a membrane is mentioned in detail, it is understood by those of ordinary skill in the art that a membrane may be excluded from the device and the device may still remain within the spirit and scope of the invention.

A top surface of third wall 24 may be non-planar, and in an embodiment may curve from a first end surface 28 to a back end surface 30 of carrier 18. First end surface 28 may be angled relative to a vertical plane disposed between the first and second end surfaces 28, 30 of carrier 18. Second end surface 30 may be substantially parallel to a vertical plane disposed between the first and second end surfaces 28, 30 of carrier 18. The top surface of third wall 24 may include one or more receptacles 36 through which one or more leashes 14 may extend in an embodiment. Receptacles 36 may be located at first end surface 28 of carrier 18. The top surface of third wall 24 may include a protrusion 32 for connection to an electrical cable 34. Protrusion 32 may be located at second end surface 30 of carrier 18. The top surface of third wall 24 may further include an elongate opening 38 through which a fluid tube 40 may extend in an embodiment. The top surface of third wall 24 may further include a portion of channels 42, 44 that extend from the top surface of third wall 24 through an exterior surface of first and second walls 20, 22, respectively, for example, as illustrated in FIG. 3.

Each of first and second walls 20, 22 may include one or more first and second connection formations 46, respectively. In the illustrated embodiment, a plurality of first and second connection formations 46 may be provided on an exterior surface of first and second walls 20, 22, respectively, that includes a channel 42, 44. First and second connection formations 46 may extend from front to back of carrier 18. In an embodiment, first and second connection formations 46 may comprise grooves or slots. Although grooves or slots are mentioned in detail, it is understood by those of ordinary skill in the art that various other connection formations may be used and remain within the spirit and scope of the invention. For example, first and second connection formations 46 may comprise one or a series of holes or openings or one or more of a series of protrusions in various embodiments. First and second formations 46 may be disposed at various vertical positions of carrier 18, and first and second connection formations 46 at various vertical positions may be substantially parallel to each other in an embodiment. Although three second connection formations 46 are illustrated in FIG. 3, it is understood by those of ordinary skill in the art that fewer or more first and second connection formations may be used and remain within the spirit and scope of the invention.

Each of first and second walls 20, 22 may further include an opening 48 through which leash 14 may extend in an embodiment. In an embodiment, the swage balls of leashes 14 may be disposed adjacent the exterior surface of first and second walls 20, 22 (i.e., at the side of carrier 18). Leashes 14 (to which the swage balls may be attached at one end) may extend through openings 48 and through receptacles 36 without being exposed to the underside of carrier 18. Leashes 14 may have sufficient material to withstand the pull force. It is understood by those of ordinary skill in the art that leashes may generally only be required on distal and proximal cell carriers as illustrated in FIG. 1. However, it is also understood by those of ordinary skill in the art that the same carrier 18 may be used in connection with mid-cells as well as distal and proximal cells without modification to the carrier in an embodiment in which the swage balls are disposed at the side of carrier 18. In another embodiment, the swage balls of leashes 14 may be disposed on the underside of carrier 18, with through-holes to receptacles 36 where leashes 14 may exit carrier 18. In this embodiment where the carrier is configured so that swage balls are disposed on the underside of carrier 18, a potting (e.g., epoxy) step may be involved and/or required in connection with mid cells (i.e., cells disposed between the distal and proximal cells). Mid cells may not generally require leashes 14, and the potting step may close the through-holes of the carrier exposed to the receiving portion 26 between first and second walls 20, 22.

Electrical cable 34 may be provided for the supply of energy. Fluid tube 40 may be provided to supply a cooling fluid to the cell 12. In an embodiment, the cooling fluid may comprise saline. However, it is understood by those of ordinary skill in the art that any number of other fluids may be used for cooling and remain within the spirit and scope of the invention. The electrical cable 34 and fluid tube 40 may extend through a manipulator 50 as shown in FIG. 1. Manipulator 50 may form a seal with body 13. The number of electrical cables, fluid tubes, or other elements disposed adjacent a top surface of third wall 24 may vary for each cell 12. Accordingly, the clearance needed between the top surface of third wall 24 and a top (e.g., covering) may need to vary for each cell 12. Rather than manufacturing cells with tops of varying heights, a universal cell may be manufactured and then paired with an upper member, such as a universal top 52.

Figure 4:
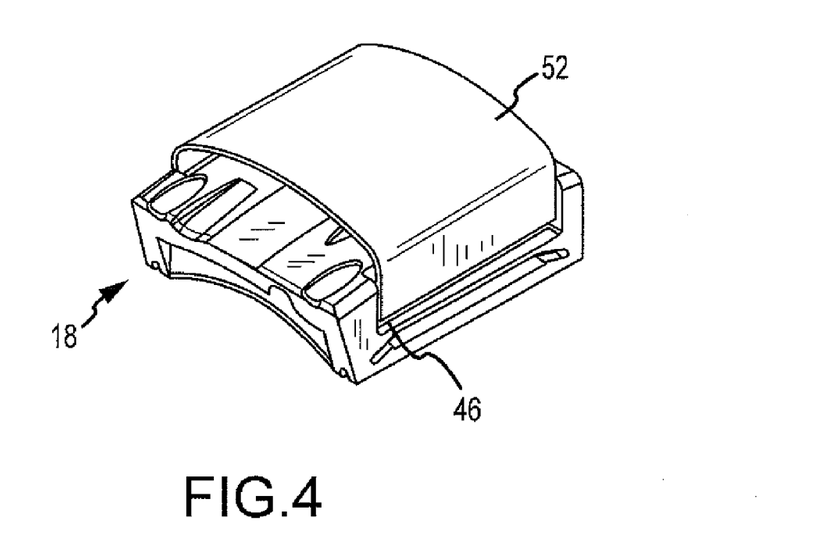
FIG. 4 is a perspective view of a carrier and top in accordance with an embodiment of the invention.

Referring now to FIG. 4, an embodiment of a universal top 52 is illustrated. Top 52 may comprise stamped sheet metal or plastic and, for some embodiments, may comprise and/or form a snap top. However, other forms of connection may be employed (e.g., pin/hole connections) and remain within the spirit and scope of the invention. Stamped sheet metal may provide more stiffness and robustness for some embodiments of the invention. Top 52 may be configured to be secured to or inserted into one of the first and second connection formations 46 located on first and second walls 20, 22 of carrier 18 in order to achieve multiple resulting cell heights. Different cell heights may be achieved by installing top 52 into different available first and second connection formations 46 on carrier 18. Accordingly, variable spaces may be created between top 52 and the top surface of third wall 24 of carrier 18. The electrical cable 34, fluid tube 40, or any number of other elements that may be connected to carrier 18 and disposed in the space between top 52 and the top surface of third wall 24 of carrier 18 may have sufficient room for storage. Top 52 may comprise a curved wall with first and second mating members (e.g., substantially horizontal legs) extending inwardly at each end of the curved wall. The first and second mating members (e.g., substantially horizontal legs) may engage first and second connection formations 46 on carrier 18, respectively thereby setting the position of top 52 relative to carrier 18 (e.g., the height of cell 12). The first and second mating members of top 52 may be configured for releasable connection to first and second connection formations 46, respectively, in an embodiment. For distal and proximal cells, top 52 may also be configured to retain the swage ball of leash 14, removing the necessity of adhering or positioning the swage ball in place.

Referring again to FIG. 1, the cells 12 of device 10 may be arranged in series and can be configured to curve and even form a substantially complete ring. Generally the first end surface 28 of a carrier 18 abuts a second end surface 30 of an adjacent carrier to promote sufficient movement to allow for shaping of device 10. However, a proximal cell may be oriented in a different direction, such that the second end surface 30 of the proximal cell abuts the second end surface 30 of an adjacent mid cell, in order to ensure that leash 14 exits carrier 18 in the right direction. This orientation results in the second end surface 30 (i.e., flat end) of a first carrier against the second end surface 30 (i.e., flat end) of a second carrier, which hinders movement and shaping of device 10. Universal carrier 18 may therefore need to be modified for a proximal cell in order to allow for the second end surface 30 of the proximal cell to be angled in order to avoid having a flat end of a proximal cell engage a flat end of an adjacent mid cell.

Figure 5:
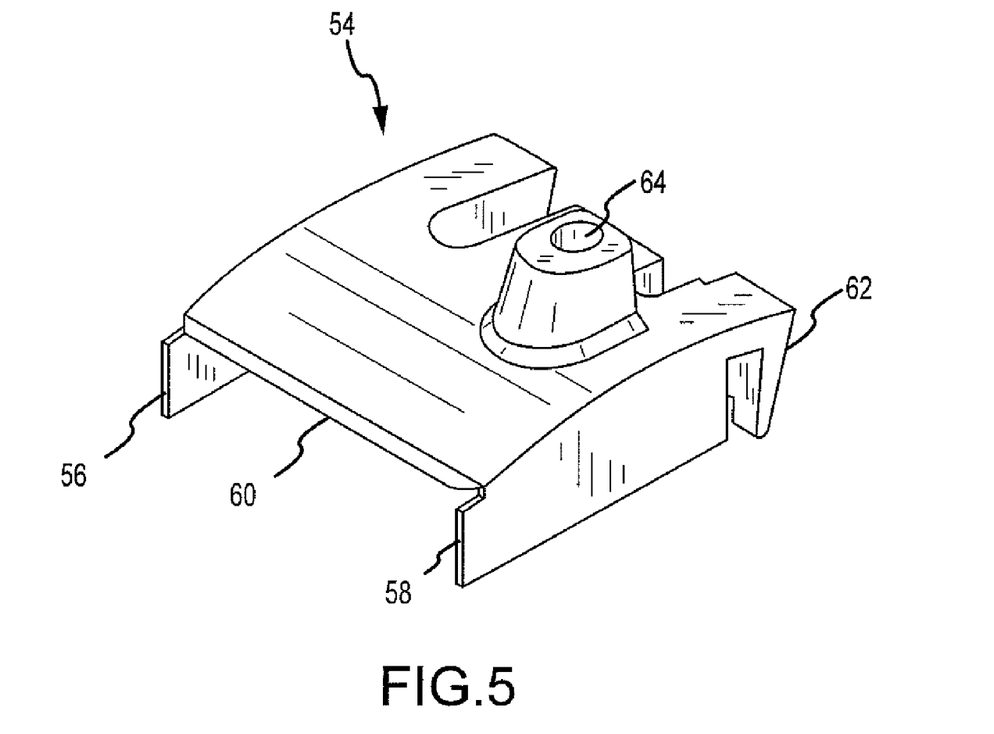
FIG. 5 is a perspective view of an adapter for a proximal cell in accordance with an embodiment of the invention.
Figure 6:
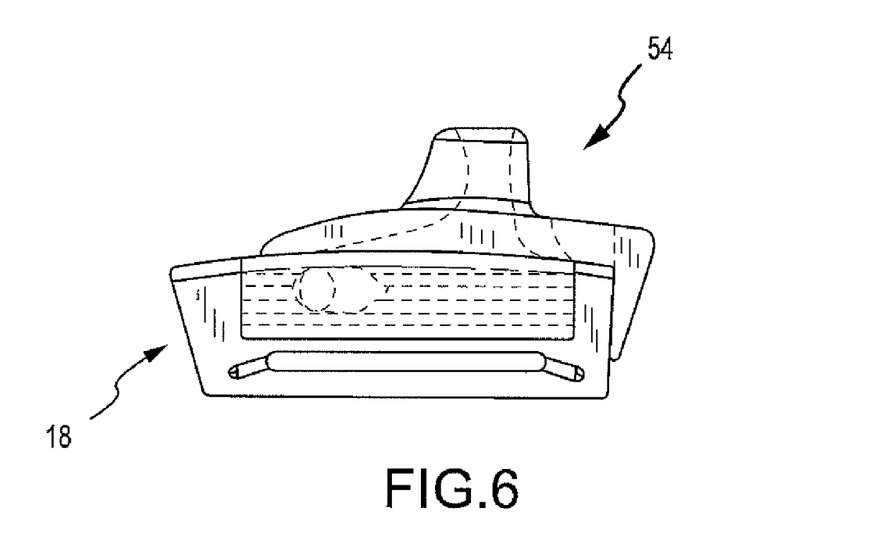
FIG. 6 is a perspective view of a carrier and an adapter for a proximal cell in accordance with an embodiment of the invention.

Referring now to FIG. 5, an embodiment of an upper member comprising a proximal adapter 54 is illustrated. Proximal adapter 54 may be provided to adapt or modify a universal cell into a suitable proximal cell, for example, by adding an angled extension on the flat side of the back end (i.e., second end surface 30) of carrier 18 and thus, allowing an angled end of a proximal cell to be adjacent a flat end of a mid-cell. Proximal adapter 54 may include a pair of side walls 56, 58 and an upper wall 60 connected therebetween. Side walls 56, 58 may be configured to be adjacent first and second walls 20, 22 of carrier 18 when adapter 54 is disposed over carrier 18 (as illustrated in FIG. 6). When adapter 54 is disposed over carrier 18, at least one of side walls 56, 58 may cover channel 42, 44 to, at least in part, retain a swage ball of leash 14 adjacent channel 42, 44. Adapter 54 may further include an extension 62 at one end. Extension 62 may be configured to extend over the second end surface 30 of carrier 18 when adapter 54 is disposed over carrier 18 (e.g., as substantially illustrated in FIG. 6). Extension 62 may be angled inwardly relative to a vertical plane disposed between the front and rear ends of adapter 54. In an embodiment, extension 62 may be inwardly angled at an angle substantially similar to the angle of the first end surface 28 of carrier 18. Adapter 54 may further include a tube 64. Tube 64 may be configured for guiding a fluid tube to carrier 18 to prevent kinking of the fluid tube and to prevent the fluid tube from taking extreme angles. Although adapter 54 is described in connection with a pair of side walls and an upper wall connected therebetween, it is understood by those of ordinary skill in the art that separate side walls 56, 58 are not required and adapter 54 may remain within the spirit and scope of the invention.

Figure 7:
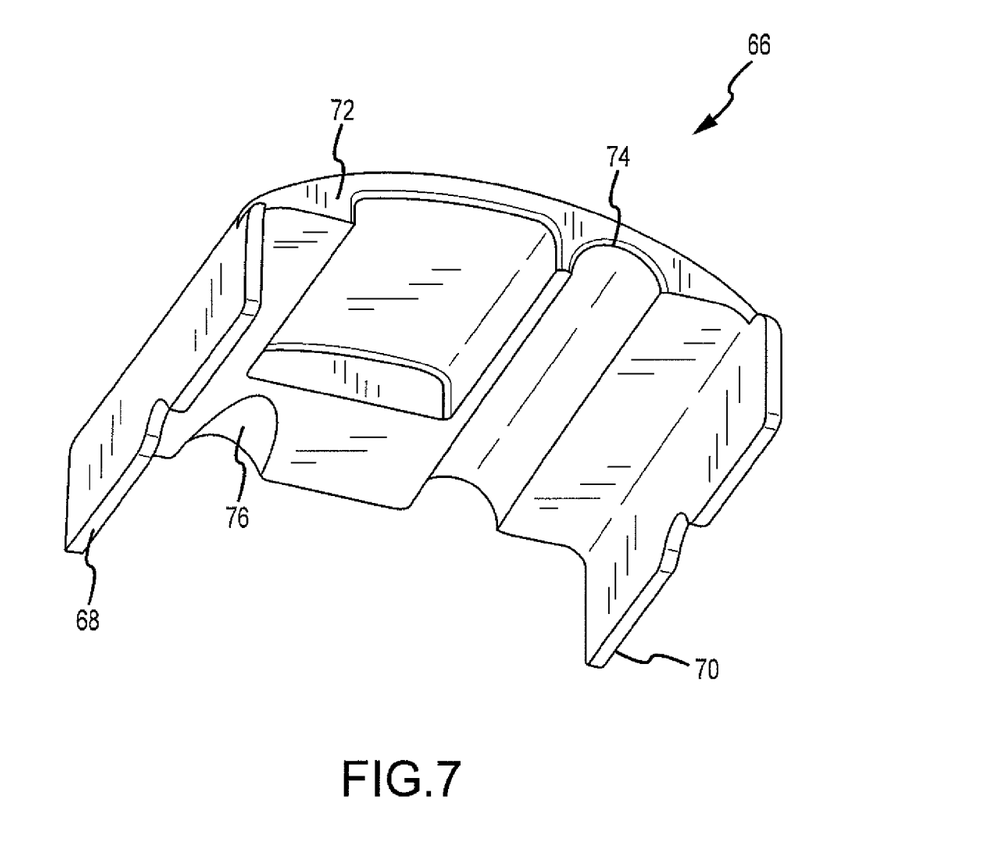
FIG. 7 is a perspective view of an adapter for a distal cell in accordance with an embodiment of the invention.

Referring now to FIG. 7, an embodiment of an upper member comprising a distal adapter 66 is illustrated. Distal adapter 66 may be provided to adapt or modify a universal cell into a suitable distal cell by adding space for attachment of leash 14. Distal adapter 66 may include a pair of side walls 68, 70 and an upper wall 72 connected therebetween. Side walls 68, 70 may be configured to be adjacent first and second walls 20, 22 of carrier 18 when adapter 66 is disposed over carrier 18. When adapter 66 is disposed over carrier 18, at least one of side walls 68, 70 may cover channel 42, 44 to, at least in part, retain a swage ball of leash 14 adjacent channel 42, 44. A top surface of upper wall 72 may be non-planar, and in an embodiment may curve from side wall 68 to side wall 70. A bottom surface of upper wall 72 may include a groove 74. Groove 74 may run substantially parallel to side walls 68, 70. Groove 74 may be provided for retaining fluid tube 40. A bottom surface of upper wall 72 may further include a receptacle 76. Receptacle 76 may be provided for retaining protrusion 32 for connection to electrical cable 34.

Although several embodiments of this invention have been described above with a certain degree of particularity, those skilled in the art could make numerous alterations to the disclosed embodiments without departing from the spirit or scope of this invention. For example, a proximal adapter may or may not be used with a carrier. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A carrier assembly comprising:
an ablation element;
a carrier comprising:
  a first wall extending from a first end surface of the carrier to a second opposing end surface of the carrier;
  a second wall extending from the first end surface of the carrier to the second end surface of the carrier, wherein the second wall is substantially parallel to the first wall;
  a third wall connecting the first wall to the second wall and wherein the first, second, and third walls define a receiving portion configured to operably receive at least a portion of the ablation element;
  a plurality of first connection formations disposed on an exterior surface of the first wall, wherein each of the plurality of first connection formations is disposed at a different vertical position of the carrier;
  a plurality of second connection formations disposed on an exterior surface of the second wall, wherein each of the plurality of second connection formations is disposed at a different vertical position of the carrier; and
an upper member configured to be disposed on the carrier, the upper member comprising a first mating member configured to be received by at least one of the plurality of first connection formations and a second mating member configured to be received by at least one of the plurality of second connection formations.

2. A carrier assembly in accordance with claim 1, wherein each of the plurality of first connection formations is substantially parallel to each other and wherein each of the plurality of second connection formations is substantially parallel to each other.

3. A carrier assembly in accordance with claim 1, wherein the carrier has an axis extending from the first end surface to the second end surface and the first end surface of the carrier is angled relative to a plane that is perpendicular to the axis and wherein the second end surface of the carrier is substantially parallel to the plane.

4. A carrier assembly in accordance with claim 3, wherein the upper member comprises an adapter configured to be disposed on the carrier, wherein the adapter comprises an angled extension that is configured to extend over the second end surface of the carrier.

5. A carrier assembly in accordance with claim 4, wherein the extension of the adapter is angled to approximately the same degree as the first end surface of the carrier.

6. A carrier assembly in accordance with claim 4, wherein the adapter further comprises a tube extending upwardly from a top of the adapter, the tube configured to guide a fluid tube connected to the carrier.

7. A carrier assembly in accordance with claim 1, wherein at least one of the first wall and the second wall includes a channel.

8. A carrier assembly in accordance with claim 1, wherein the upper member comprises a top configured for connection to the carrier.

9. A carrier assembly in accordance with claim 8, wherein the first mating member comprises a first inwardly extending leg and wherein the second mating member comprises a second inwardly extending leg.

10. A carrier assembly in accordance with claim 1, wherein the first mating member is configured for connection to any of the plurality of first connection formations disposed on the carrier and the second mating member is configured for connection to any of the plurality of second connection formations disposed on the carrier to provide a variable space between the carrier and the upper member.

11. A carrier assembly in accordance with claim 1, wherein the third wall of the carrier further comprises a first opening configured to receive a leash and a second opening configured to receive a fluid tube.

12. A carrier assembly in accordance with claim 11, further comprising a leash having a swage ball at one end, wherein the leash extends through the first opening.

13. A device for epicardial ablation, comprising:
a plurality of ablation elements;
a plurality of carriers disposed adjacent to each other, wherein each carrier includes:
  a first wall extending from a first end surface to a second opposing end surface;
  a second wall extending from the first end surface to the second end surface, wherein the second wall is substantially parallel to the first wall;
  a third wall connecting the first wall to the second wall and wherein the first, second, and third walls define a receiving portion configured to operably receive at least a portion of one of the plurality of ablation elements;
  a plurality of first connection formations disposed on an exterior surface of the first wall, wherein each of the plurality of first connection formations is disposed at a different vertical position on the first wall; and
  a plurality of second connection formations disposed on an exterior surface of the second wall, wherein each of the plurality of second connection formations is disposed at a different vertical position on the second wall; and
a plurality of upper members configured to be disposed on the plurality of carriers, wherein each upper member includes a first mating member configured to be received by at least one of the plurality of first connection formations and a second mating member configured to be received by at least one of the plurality of second connection formations.

14. A device in accordance with claim 13, wherein each of the plurality of upper members is configured for connection to any of the plurality of first connection formations disposed on each of the plurality of carriers and any of the plurality of second connection formations disposed on each of the plurality of carriers to provide a variable space between each of the plurality of carriers and each of the plurality of upper members.

15. A device in accordance with claim 14, wherein the device further comprises at least one of an electrical cable and a fluid tube, and the electrical cable or fluid tube is connected to at least one of the plurality of carriers and is disposed in the space between at least one of the plurality of carriers and at least one of the plurality of upper members.

16. A device in accordance with claim 13, wherein the device is configured to curve and form a substantially complete ring.

17. A device in accordance with claim 13, wherein one of the plurality of upper members comprises an adapter configured to be disposed on one of the plurality of carriers that is located at a proximal end of the device, wherein the adapter comprises an angled extension that is configured to extend over the second end surface of the one of the plurality of carriers that is located at the proximal end of the device.

18. A device in accordance with claim 17, wherein an orientation of the one of the plurality of carriers that is located at the proximal end of the device is different from an orientation of the remainder of the plurality of carriers.

19. A device in accordance with claim 13, wherein one of the plurality of upper members comprises an adapter configured to be disposed on the one of the plurality of carriers that is located at the distal end of the device, wherein the adapter comprises at least one wall with a groove configured to receive a tube.

* * * * *